(12) United States Patent  
Rietzel

(10) Patent No.: US 7,838,852 B2  
(45) Date of Patent: Nov. 23, 2010

(54) MEDICAL RADIATION APPARATUS

(75) Inventor: Eike Rietzel, Darmstadt (DE)

(73) Assignee: Siemens Aktiengesellschaft, Munich (DE)

( * ) Notice: Subject to any disclaimer, the term of this patent is extended or adjusted under 35 U.S.C. 154(b) by 194 days.

(21) Appl. No.: 11/636,670

(22) Filed: Dec. 8, 2006

(65) Prior Publication Data

US 2007/0167748 A1 Jul. 19, 2007

Related U.S. Application Data

(60) Provisional application No. 60/748,849, filed on Dec. 9, 2005.

(30) Foreign Application Priority Data

Dec. 9, 2005 (DE) ........................ 10 2005 058 871

(51) Int. Cl.  
*A61N 5/10* (2006.01)

(52) U.S. Cl. ............... 250/492.3; 250/363.01; 250/306; 250/307; 250/308; 250/310; 378/4; 378/8; 378/20; 378/41; 378/62; 600/1; 600/407; 600/409; 600/410; 600/425; 715/839

(58) Field of Classification Search ............ 250/363.01, 250/363.02, 363.04, 363.07, 363.09, 306, 250/307, 308, 309, 310, 492.1, 492.3, 396 R; 600/1, 407, 409, 410, 411, 416, 425, 427, 600/439; 378/4, 8, 20, 41, 42, 62, 65; 715/839  
See application file for complete search history.

(56) References Cited

U.S. PATENT DOCUMENTS

| | | | | |
|---|---|---|---|---|
| 5,039,867 A | * | 8/1991 | Nishihara et al. | 250/492.3 |
| 5,538,494 A | * | 7/1996 | Matsuda | 600/1 |
| 5,748,700 A | * | 5/1998 | Shepherd et al. | 378/65 |
| 6,104,779 A | * | 8/2000 | Shepherd et al. | 378/65 |
| 6,219,403 B1 | * | 4/2001 | Nishihara | 378/65 |
| 6,222,544 B1 | * | 4/2001 | Tarr et al. | 715/839 |
| 6,725,078 B2 | * | 4/2004 | Bucholz et al. | 600/410 |
| 6,862,469 B2 | * | 3/2005 | Bucholz et al. | 600/411 |

(Continued)

FOREIGN PATENT DOCUMENTS

DE 35 02 776 A1 7/1986

(Continued)

OTHER PUBLICATIONS

Eike Rietzel, George T. Y. Chen, Noah C. Choi, and Christopher G. Willet, "Four-Dimensional Image-Based Treatment Planning: Target Volume Segmentation and Dose Calculation in the Presence of Respiratory Motion", Int. J. Radiation Oncology Biol. Phys.2005, pp. 1535-1550, vol. 61, No. 5, Elsevier Inc., USA.

(Continued)

*Primary Examiner*—Robert Kim  
*Assistant Examiner*—Michael Maskell

(57) ABSTRACT

A medical radiation apparatus has a beam source and a deflection apparatus, which can be activated by means of a data processing device according to a radiation schedule generated using a recording of tissue to be irradiated produced using a medical imaging diagnosis device, said data processing device being set up for data purposes such that characteristics of the radiation acting on the tissue according to different irradiation scenarios can be visualized in a common display.

14 Claims, 2 Drawing Sheets

U.S. PATENT DOCUMENTS

| | | | |
|---|---|---|---|
| 6,912,265 B2 * | 6/2005 | Hebecker et al. | 378/4 |
| 6,993,112 B2 * | 1/2006 | Hesse | 378/65 |
| 7,035,371 B2 * | 4/2006 | Boese et al. | 378/41 |
| 7,050,531 B2 * | 5/2006 | Hebecker et al. | 378/8 |
| 7,199,382 B2 * | 4/2007 | Rigney et al. | 250/492.1 |
| 7,257,191 B2 * | 8/2007 | Sommer | 378/65 |
| 7,567,694 B2 * | 7/2009 | Lu et al. | 382/128 |
| 7,609,809 B2 * | 10/2009 | Kapatoes et al. | 378/65 |
| 2003/0147495 A1 * | 8/2003 | Kato et al. | 378/65 |
| 2003/0164459 A1 * | 9/2003 | Schardt et al. | 250/492.3 |
| 2004/0199068 A1 * | 10/2004 | Bucholz et al. | 600/411 |
| 2005/0116172 A1 * | 6/2005 | Trinkaus et al. | 250/363.02 |

FOREIGN PATENT DOCUMENTS

| | | |
|---|---|---|
| DE | 100 25 913 A1 | 12/2001 |
| DE | 101 51 987 A1 | 5/2003 |
| JP | 11290466 A | 10/1999 |
| WO | WO 03/038725 * | 5/2003 |

OTHER PUBLICATIONS

Radhe Mohan, Xiaodong Zhang, He Wang, Yixiu Kang, Xiaochun Wang, Helen Liu, K. Kian Ang, Deborah Kuban and Lei Dong, "Use of Deformed Intensity Distributions for On-Line Modification of Image-Guided IMRT to Account for Interfractional Anatomic Changes", Int. J. Radiation Oncology Biol. Phys, 2005, pp. 1258-1266, vol. 61, No. 4, Elsevier Inc., USA.

Isaac Rosen, H. Helen Liu, Nathan Childress and Zhongxing Liao, "Interactively Exploring Optimized Treatment Plans", Int. J. Radiation Oncology Biol.. Phys., 2005, pp. 570-582, vol. 61, No. 2, Elsevier Inc., USA.

* cited by examiner

MEDICAL RADIATION APPARATUS

CROSS REFERENCE TO RELATED APPLICATIONS

The present application claims the benefit of the provisional patent application filed on Dec. 9, 2005, and assigned application No. 60/748,849. The present application also claims priority of German application No. 10 2005 058 871.9 filed on Dec. 9, 2005. Both of the applications are incorporated by reference herein in their entirety.

FIELD OF THE INVENTION

The invention relates to a medical radiation apparatus as well as a method for setting operating parameters of a medical radiation apparatus.

BACKGROUND OF THE INVENTION

A medical radiation apparatus is known for example from DE 35 02 776 A1. This radiation apparatus comprises a linear accelerator as the radiation source and what is known as a simulator with an x-ray tube for precise patient positioning.

A radiation apparatus operating with particle beams, specifically ion beams, is known from DE 100 25 913 A1, with provision being made for specifying the energy and ion dosage in a radiation schedule, thereby defining the penetration depth of the ion beam and the quantity of radiation. A PET camera is installed in the radiation area to monitor radiation.

With medical radiation apparatuses every effort is generally made only to expose the tissue to be treated to the radiation and to protect the surrounding tissue as far as possible. This objective can be achieved with particle radiation due to its inverse dosage profile with particularly good exposure. Unlike electromagnetic radiation, particles typically emit the most energy at the end of their range. This characteristic of particle beams extends the options for treating tumors, which are adjacent to high-risk organs. It is particularly important in such an instance to draw up and comply precisely with a radiation schedule. It should be noted that it is possible for the form and density of the tissue to be irradiated to change significantly during the course of radiation therapy, in particular due to the effect of the radiation. It may therefore become necessary to draw up a new radiation schedule during the radiation therapy.

SUMMARY OF THE INVENTION

The object of the invention is to specify a medical radiation apparatus, in particular one operating with particle radiation, which is particularly suited to tailoring the radiation to changing conditions during the course of the therapy. It is a further object of the invention to specify a method, with which operating parameters of a medical radiation apparatus can be tailored to changing therapeutic requirements as the therapy progresses.

According to the invention this object is achieved by a medical radiation apparatus and a method with the features of the claims. Embodiments and advantages set out below in respect of the device also apply analogically to the method and vice versa.

The radiation apparatus comprises a beam source, in particular a particle beam source, and a deflection apparatus, which refers to any apparatus, which influences the radiation, in particular the energy and direction of the particles, in a controlled manner. A data processing device is provided to activate the radiation apparatus, said data processing device setting operating parameters of the beam source and the deflection unit according to a radiation schedule. The radiation schedule has been generated beforehand on the basis of a recording of the tissue to be irradiated, produced using a medical imaging diagnosis device, in particular a computed tomography device. The data processing device is programmed such that a number of characteristics of the radiation acting on the tissue can be visualized in a common display. The characteristics are thereby determined for successive radiation operations based on different irradiation scenarios. The display in particular includes a past-related irradiation scenario and a future-related irradiation scenario. Irradiation scenarios are in particular determined taking into account the same radiation type and preferably also the same radiation source. The radiation characteristics that can be displayed with the aid of the data processing device in particular include the energy deposited in the tissue. The radiation range can also be displayed. The graphic display of characteristics of the radiation to be applied according to the radiation schedule is advantageously incorporated in a two or three-dimensional display of the tissue to be irradiated.

The first irradiation scenario mentioned is based on a first recording of the tissue to be irradiated produced using the medical imaging diagnosis device, said recording having been obtained before the radiation therapy started. A first radiation schedule has been generated on the basis of this recording with computer assistance. The operating parameters of the medical radiation apparatus corresponding to this radiation schedule are initially not modified. Rather a second irradiation scenario is considered with these operating parameters, which is not based on the original recording of the tissue to be irradiated but a more recent recording obtained after the tissue has been irradiated.

The changed geometry and/or composition of the tissue to be irradiated results in a modified characteristic, in particular range, of the radiation. This characteristic is inserted into a display of the original characteristic with computer assistance. In this step therefore a second radiation schedule is simulated, with only the form and/or nature of the irradiated tissue being modified initially. The operator using the radiation apparatus and the data processing system is able, as a result of the second irradiation scenario, to produce an image of the effects of the radiation under the changed conditions, with the modified effects being contrasted visually in a direct manner with the effects according to the original radiation schedule.

In a next step the operator is able to simulate a scenario with modified parameter settings for the radiation apparatus. It is particularly advantageous here for the operator to be able to use as a basis geometrically displayable radiation characteristics, in particular ranges and/or dosage distributions. The data processing system uses modified characteristics that can be predetermined by the user to determine appropriate new operating parameters for the radiation apparatus. Irradiation can then be simulated using the new parameter settings, it being possible again to display the results in contrast to the results of irradiation already carried out and/or another scenario. The operator is therefore able to adapt the radiation schedule very quickly and appropriately to changed conditions.

According to a preferred embodiment the radiation characteristics are visualized using the volume rendering (VR) method and/or the surface rendering (SR) method. The VR method allows a semitransparent display of structures and is described for example in the Siemens AG publication "electro medica", volume 1, 2003, pages 50-57. Further information, also relating to the SR method, is contained in the dissertation "Dreidimensionale Darstellung der Hirnnerven V-VIII mittels virtueller Zistemoskopie" (Three-dimensional display of the cranial nerves V-VIII using virtual cisternoscopy) (Christian Nikolaus Heine, Medical Fakultät der Charité—Universitätsmedizin Berlin, 2004). The VR method allows differences between different irradiation scenarios to be displayed in a three-dimensional manner over the entire relevant volume. Additionally or alternatively a layer by layer comparative display is also possible.

The invention has the particular advantage that a comparative visualization covering different irradiation scenarios allows the operator to set radiation schedule parameters very quickly and in an uncomplicated manner.

BRIEF DESCRIPTION OF THE DRAWINGS

An exemplary embodiment of the invention is described in more detail below with reference to a drawing showing simplified illustrations, wherein.

Corresponding elements or parameters are marked with the same reference characters in all the figures.

DETAILED DESCRIPTION OF THE INVENTION

Figure 1:
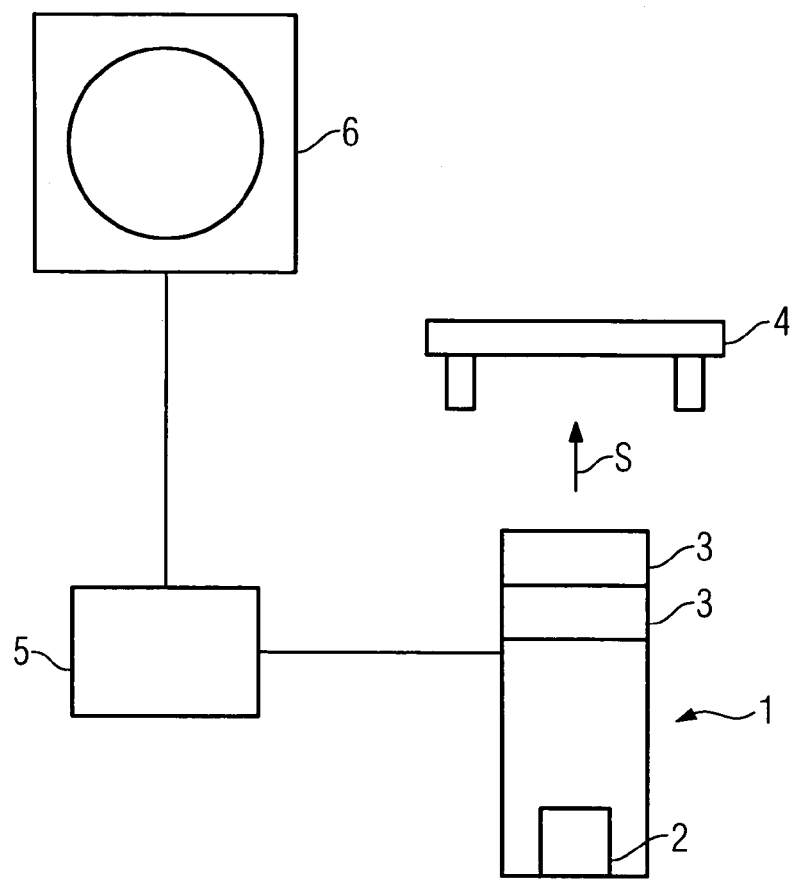
FIG. 1 shows a medical radiation apparatus and a medical imaging diagnosis device linked thereto for data purposes.

FIG. 1 shows a symbolized diagram of a medical radiation apparatus 1, comprising a beam source 2, specifically a particle beam source, and an apparatus generally referred to as a deflection apparatus 3 to influence the energy and/or direction of the radiation. The beam direction of the particle beam is shown as S. A patient (not shown) with tissue to be irradiated is located on a patient support 4. The irradiation operation is carried out according to a radiation schedule, which predetermines parameter settings of the beam source 2 and the deflection apparatus 3 and by association parameters of the particle radiation such as beam geometry, particle energy and radiation dosage. Storage of the data required to implement the radiation schedule and activation of the beam source 2 and deflection apparatus 3 are effected by means of a data processing device 5, which is also connected for data purposes to a medical imaging diagnosis device 6, specifically a computed tomograph. Alternatively the medical imaging diagnosis device 6 can be a magnetic resonance device for example.

A recording of the tissue to be irradiated and the surrounding tissue regions of the patient obtained using the medical imaging diagnosis device 6 serves as the basis for drawing up the radiation schedule. The data processing device 5 allows a three-dimensional display of the tissue to be irradiated.

Figure 2:
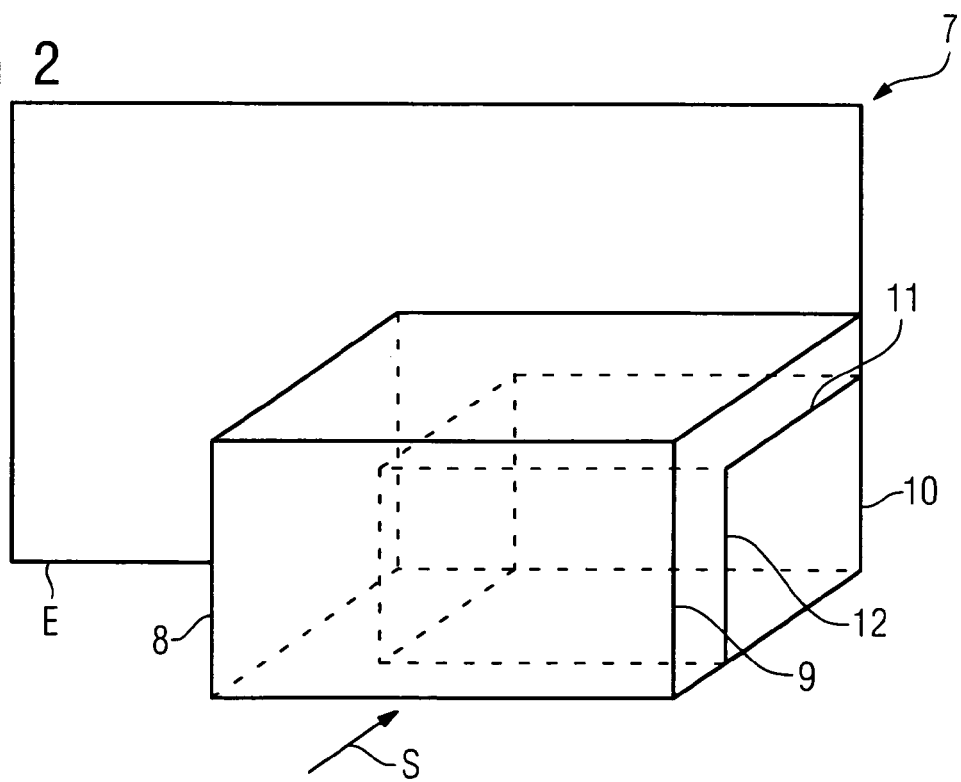
FIG. 2 shows a volume to be irradiated using the medical radiation apparatus according to FIG. 1.

FIG. 2 shows a roughly schematic display 7 of possible forms of a volume to be irradiated as can be reproduced using the data processing device 5. A rectangular first volume 8 in the display is exposed to particle radiation striking in the beam direction S according to the radiation schedule. This first volume 8 may correspond to the shape of a tumor, detected with the aid of the medical imaging diagnosis device 6. The minimum and maximum energy of the particles emitted by the beam source 2 are dimensioned such that the particles emit their energy solely in the first volume 8 bounded by a proximal boundary surface 9 and a distal boundary surface 10 with the best possible exposure. The dosage distribution of the radiation deposited by means of the beam source 2 can also be shown in a three-dimensional view in the display 7. Different dosages are hereby indicated using different colors for example.

Clarity is enhanced when only boundary surfaces, in particular the proximal boundary surface 9 and the distal boundary surface 10, are visualized in the display 7. If the boundary surfaces 9, 10 correspond exactly to surfaces of the tissue to be irradiated, which should ideally be the case, the view shown in FIG. 2 results. The volume rendering method and the surface rendering method are particularly suitable for this. Both methods represent reconstruction techniques, with the surface rendering method generally using less than 10% of the image data, while the volume rendering method uses almost all the data and is much less likely to form artifacts. The boundary surfaces 9, 10 shown in the display 7 correspond to what is known as the proximal or distal edge of the particle radiation.

Irradiation of the tumor causes its volume to reduce over time, as can be diagnosed with the aid of the diagnosis device 6. The size of the regressed tumor corresponds to a second volume 11, shown with a broken line in the display 7. While the position of the distal boundary surface 10 remains the same compared with the first volume 8, specifically in a plane E, the second volume 11 has a proximal boundary surface 12, which is displaced in the beam direction S. This displacement is to be taken into account in a modified radiation schedule tailored to the smaller tumor. The operator of the radiation apparatus 1 and data processing device 5 is able to allow the simulation of characteristics, in particular dosage distributions and the position of boundary surfaces 9, 10, 12, of the radiation.

If during simulation it is assumed for example that only the second volume 11 is to be irradiated, maintaining the parameter settings of the original radiation schedule, radiation boundary surfaces would be overlaid in the display 7, which are significantly outside the second volume 11. For the operator this would be a clear indication that the parameter settings have to be changed. The simulation can then be carried out once again with tailored parameter settings. The data processing device 5 is advantageously programmed to find a parameter setting for the beam source 2 and the deflection apparatus 3 that is suitable for particle radiation automatically for a predetermined volume 8, 11 to be irradiated. In a similar manner to the first volume 8, in the instance of the second volume 11 radiation boundary surfaces 10, 12 are inserted automatically into the three-dimensional display 7 as well as surfaces of the volume 8 itself. In the idealized exemplary embodiment according to FIG. 2 the boundary surfaces 10, 12 also correspond exactly to surfaces of the volume 11 in the case of the second, smaller volume 11. Generally the simulation is carried out automatically for every beam direction S, in other words for every entry path.

Figure 3:
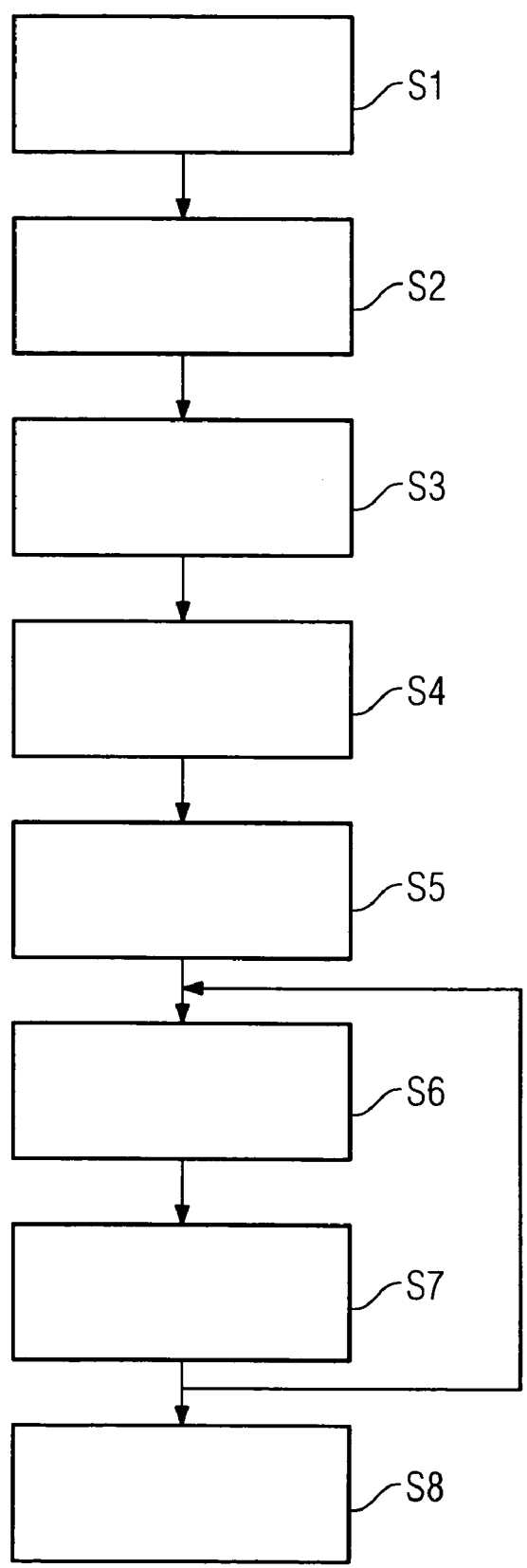
FIG. 3 shows a flow diagram of a method for setting operating parameters for the medical radiation apparatus according to FIG. 1.

The process of setting and adjusting operating parameters of the radiation apparatus 1 is described below with reference to FIG. 3:

In a first step S1 a three-dimensional recording of the tissue to be irradiated is produced using the medical imaging diagnosis device 6. In the second step S2 a first radiation schedule is drawn up on the basis of this recording with computer assistance. Irradiation is carried out in the third step S3 according to this schedule. Between two irradiation operations, referred to as fractions, in a fourth step S4 a recording is again taken of the tissue to be irradiated with the aid of the diagnosis device 6. This second recording (see second volume 11 in FIG. 2) is used in a fifth step S5 to simulate the results of a second radiation schedule, in which the parameter settings of the radiation apparatus 1 initially remain unchanged but the diagnosed changes in the tissue to be irradiated are taken into account. In the next, sixth step S6 the results of the simulation, in other words characteristics of the irradiation carried out or simulated according to the different scenarios, are displayed simultaneously in a common display 7 (FIG. 2), allowing direct comparison of the different results. In the next step S7 the parameter settings of the radiation apparatus 1 are changed in a new simulation, to show the results again in a display 7 (step S6). This process is repeated a number of times, if necessary, until in step S8 irradiation continues according to an updated radiation schedule, thereby ensuring conformity of the irradiation.

The invention claimed is:

1. A medical radiation apparatus for irradiating a tissue of a patient during a course of a therapy, comprising:
    a medical imaging diagnosis device that generates a recording of the tissue to be irradiated;
    a beam source that generates a radiation;
    a deflection apparatus that directs the radiation to the tissue;
    a data processing device that activates the beam source and the deflection apparatus according to a radiation schedule of the therapy based on the recording, wherein the data processing device is configured to determine a plurality of original characteristics of radiation acting on the tissue, the data processing device being further configured to determine at least one modified characteristic of subsequent radiation acting on the tissue, the modified characteristics being determined by the data processing device based on a plurality of different irradiation scenarios of irradiation operations at different times, wherein the plurality of different irradiation scenarios comprises a first irradiation scenario based on the generated recording of the tissue to be irradiated, and further includes a simulated second irradiation scenario based on a changed physical condition of the tissue subsequent to applying to the tissue a first irradiation constructed in accordance with said first irradiation scenario, the data processing device configured to generate an image consisting of boundary surfaces corresponding to a distal boundary and to a proximate boundary relative to a beam of radiation from the beam source, the image arranged to visually contrast a radiation spatial distribution in the changed tissue with respect to a radiation spatial distribution resulting from the first irradiation applied to the tissue; and
    a display device coupled to the data processing device to simultaneously display the radiation spatial distribution in the changed tissue with respect to the radiation spatial distribution resulting from the first irradiation, wherein a displacement of the proximate boundary in a direction of the radiation beam is defined in a displayed image, the boundary displacement allows an operator to adapt the radiation therapy by way of a respective adjustment to at least one operating parameter to account for the changed physical condition of the tissue as the tissue undergoes the radiation therapy.

2. The medical radiation apparatus as claimed in claim 1, wherein the beam source is a particle beam source.

3. The medical radiation apparatus as claimed in claim 1, wherein the different irradiation scenarios comprise different geometries of the tissue.

4. The medical radiation apparatus as claimed in claim 3, wherein the geometries of the tissue change over a period of time.

5. The medical radiation apparatus as claimed claim 1, wherein the characteristic of the radiation acting on the tissue is a dosage distribution of the radiation.

6. The medical radiation apparatus as claimed in claim 1, wherein the characteristic of the radiation acting on the tissue is displayed together with the tissue on the display device.

7. The medical radiation apparatus as claimed in claim 1, wherein a plurality of boundary surfaces of the radiation are displayed on the display device.

8. The medical radiation apparatus as claimed in claim 7, wherein the boundary surfaces of the radiation are calculated based on a minimum and a maximum energy of the radiation.

9. The medical radiation apparatus as claimed in claim 1, wherein the characteristic of the radiation is displayed by a volume rendering method.

10. The medical radiation apparatus as claimed in claim 1, wherein the characteristic of the radiation is displayed by a surface rendering method.

11. The medical radiation apparatus as claimed in claim 1, wherein the characteristic of the radiation is displayed layer by layer.

12. A method for setting up an operating parameter for a medical radiation apparatus in a course of a therapy, comprising:
    generating a first imaging recording of a tissue of a patient to be irradiated;
    creating a first radiation schedule comprising the operating parameter based on the first imaging recording of the tissue;
    defining a first characteristic of the radiation acting on the tissue according to the first radiation schedule;
    irradiating the tissue according to the first radiation schedule for a first irradiation;
    generating a second imaging recording of the tissue showing a changed geometry and/or composition of the tissue after the first irradiation;
    simulating a second radiation schedule based on the second imaging recording of the tissue after the first irradiation;
    defining a second characteristic of the radiation to act on the tissue according to the simulation;
    generating an image consisting of boundary surfaces corresponding to a distal boundary and to a proximate boundary relative to a beam of radiation from the beam source;
    simultaneously displaying the first characteristic and the second characteristic of the radiation in a common display device, wherein the displaying includes visually contrasting in a displayed image a radiation spatial distribution in the changed tissue with respect to a radiation spatial distribution resulting from the first irradiation applied to the tissue;
    defining in the displayed image a displacement of the proximate boundary in a direction of the radiation beam, the displacement of the proximate boundary allowing an operator to adapt the radiation therapy by way of a respective adjustment to at least one operating parameter of the medical radiation apparatus to account for the changed geometry and/or composition of the tissue as the tissue undergoes the radiation therapy;
    changing the operating parameter according to the display;
    updating the second radiation schedule based on the changed operating parameter;
    modifying the second characteristic of the radiation according to the updated second radiation schedule; and irradiating the tissue according to the updated second radiation schedule for a second irradiation.

13. The method as claimed in claim 12, wherein the first and the second imaging recordings of the tissue are generated by a medical imaging diagnosis device using a computed tomograph method.

14. The method as claimed in claim 12, wherein the first and the second radiation schedules are defined based on a density distribution of the tissue changing over a period of time.

* * * * *